United States Patent
Kim et al.

[11] Patent Number: 6,029,086
[45] Date of Patent: Feb. 22, 2000

[54] AUTOMATIC THRESHOLD SENSITIVITY ADJUSTMENT FOR CARDIAC RHYTHM MANAGEMENT DEVICES

[75] Inventors: Jungkuk Kim, Roseville; Jesse W. Hartley, Lino Lakes; Qingsheng Zhu, Little Canada, all of Minn.

[73] Assignee: Cardiac Pacemakers, Inc., St. Paul, Minn.

[21] Appl. No.: 09/094,773

[22] Filed: Jun. 15, 1998

[51] Int. Cl.[7] ................................................ A61N 1/362
[52] U.S. Cl. .................................................................. 607/9
[58] Field of Search ..................................... 609/9, 14, 17

[56] References Cited

U.S. PATENT DOCUMENTS

| | | |
|---|---|---|
| 4,779,617 | 10/1988 | Whigham ................................. 607/9 |
| 5,365,932 | 11/1994 | Greenhut ................................. 600/508 |
| 5,564,430 | 10/1996 | Jacobson et al. ....................... 600/510 |
| 5,755,738 | 5/1998 | Kim et al. . |

*Primary Examiner*—William E. Kamm
*Assistant Examiner*—Carl H. Layno
*Attorney, Agent, or Firm*—Nikolai, Mersereau & Dietz, P.A.

[57] ABSTRACT

An implantable cardiac rhythm management device includes a controller adapted to receive digitized electrocardiogram signals from leads placed on or in the heart. The device also incorporates an autosense algorithm which automatically adjusts the sensing threshold dependent upon an average or maximum amplitude of noise detected during a period following a sensed cardiac depolarization. The sensing threshold is automatically set on a beat-to-beat basis at a level such that the signal to noise ratio exceeds a preset value.

21 Claims, 6 Drawing Sheets

AUTOMATIC THRESHOLD SENSITIVITY ADJUSTMENT FOR CARDIAC RHYTHM MANAGEMENT DEVICES

BACKGROUND OF THE INVENTION

I. Field of the Invention

This invention relates generally to an apparatus for stimulating cardiac tissue, and more particularly to an implantable cardiac rhythm management device and method for automatically adjusting the sensing threshold. The sensing threshold of the cardiac rhythm management device is automatically adjusted on a beat by beat basis following a predetermined period and the adjustment is made dependent upon an amplitude of an intrinsic beat and upon an amplitude and frequency of noise occurring during the period.

II. Discussion of the Prior Art

For the most part, prior art implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implantable cardiac rhythm management device. Typically, the signals emanating from the sense amplifier are applied to one input of a comparator circuit whose other input is connected to a source of reference potential. Only when an electrogram signal from the sense amplifier exceeds the reference potential threshold will it be treated as a cardiac paced or sensed beat. The source reference potential may be referred to as a sensing threshold.

In the case of a programmable cardiac rhythm management device, the prescribing physician can change the threshold potential of the comparator, but in spite of the flexibility which the programmable threshold offers, malsensing of cardiac depolarization will still occur frequently enough to result in patient discomfort. This may be due to the fact that cardiac depolarization events (intrinsic beats) can result in widely different peak amplitudes, depending on patient activity, body position, drugs being used, etc. Lead movement and noise may further impede the detection of cardiac depolarization events. Noise sources may include environmental noise, such as, 50 or 60 Hz power line noise, muscle noise, motion artifacts, baseline wander and T-waves. When the peak amplitudes associated with cardiac depolarization events become too small relative to a programed threshold, or when noise levels in the electrocardiogram approach the sensing threshold, the likelihood of false sensing increases. The peak amplitudes of the electrogram signals associated with cardiac depolarization events is also quite dependent on the type of lead being used and whether the electrodes on the lead abut cardiac tissue or are floating within a cardiac chamber. Thus, it is desirable that an implantable pacemaker or defibrillator be able to automatically adjust the sensing threshold on a beat by beat basis as the patient's activity, body position, drugs being used, etc. changes. It would also be desirable for the rhythm management device to use active or passive fixation bipolar and unipolar leads and/or single pass VDD or DDD leads.

The Jacobson et al. U.S. Pat. No. 5,564,430 describes an automatic sensing threshold control for implantable cardiac rhythm management devices. In the device described by Jacobson et al., the sensing threshold is set according to the amplitude of both sensed signals corresponding to cardiac activity and to sensed noise. The amplitude of sensed noise is measured during a noise interval that follows an absolute refractory period. In many cases there is a need for the sensing threshold to be adjusted prior to the end of both a refractory period and a noise interval, however, the Jacobson device does not provide for such a circumstance. After both independent intervals time out, the Jacobson et al. algorithm adjusts the threshold such that the sensing threshold is substantially below the peak amplitude of sensed cardiac activity, but above the noise level. In accordance with Jacobson et al., the sensing threshold is initially set at a predetermined fraction (one-fourth) of a measured sensed depolarization signal. An absolute refractory period following the occurrence of a sensed signal is provided for, and then, following the absolute refractory period is an established "noise refractory period". If a sensed signal that exceeds the set sensing threshold is detected during the noise refractory period, the noise refractory period is restarted and the sensing threshold is incremented by increasing its level by about 0.2 millivolts such that the resulting sensing threshold will ultimately be set above the noise amplitude. In fluctuating noise environments, such incrementation may not effectively adjust the sensing threshold.

While the method described in the Jacobson et al. patent may prove satisfactory for robust electrocardiogram signals, it is less than satisfactory for low amplitude electrocardiogram signals, such as may be associated with the use of lead pacing systems or low amplitude atrial electrocardiogram signals derived from conventional leads. A further drawback of the algorithm described in the Jacobson et al. '430 patent is the noise detection utilizing retriggerable noise refractory windows. If noise signals are stable in amplitude, the algorithm will detect noise levels properly. However, those skilled in the art appreciate that noise does not behave in that fashion. The amplitude of the noise level keeps changing and often includes impulsive noise excursions. It is, therefore, difficult for a noise refractory window to detect episodes of that type. Also, the delay in adequate threshold adjustment and the 0.2 millivolt buffering between noise and the sensing threshold may not be sufficient in many situations.

A need, therefore, exists for an autosense algorithm for incorporation into a cardiac rhythm management device that will provide automatic adjustment of the sensing threshold, taking into account the amplitude of noise (detected during a predetermined period), and the amplitude of electrocardiogram signals associated with sensed events. The present invention meets that need.

SUMMARY OF THE INVENTION

The present invention provides a method and apparatus for automatically adjusting a sensing threshold (ST) in a cardiac rhythm management device as the amplitude of cardiac depolarization and noise fluctuate. The rhythm management device may include a sensing amplifier for amplifying and filtering electrocardiogram signals picked up by electrodes that are coupled to the sense amplifier by a pacing lead. Also included is a power supply, peak detector, timing circuit, controller coupled to receive the sensed electrogram signals and means controlled by the controller for applying cardiac stimulation pulses to a patient's heart. The stimulation pulses are applied in response to control signals from the controller.

The controller and components contained therein or coupled thereto detect and distinguish cardiac depolarization deflections and noise deflections from the electrocardiogram signal. A peak detector is utilized to determine the amplitudes of the cardiac depolarization deflections and noise deflections. From the detected deflections, the amplitudes of cardiac depolarization deflections and noise deflections are determined and the sensing threshold is adjusted dependent upon the amplitude of the cardiac depolarization and noise. In one embodiment, once a cardiac depolarization is detected, a period is initiated and the amplitude of each deflection associated with noise is measured and the number of deflections counted during at least a portion of the predetermined period. The sensing threshold value is immediately calculated and adjusted taking into account the determined amplitude of the cardiac depolarization, either the maximum or average measured amplitude of noise, and the number of deflections counted during the selected portion of the predetermined period.

In another embodiment of the invention, once a cardiac depolarization deflection is detected, a predetermined period (for example, the refractory period) is initiated and then the noise level is "measured" during at least a portion of the period. The noise level is "measured" by counting the number of noise deflections exceeding the sensing threshold and estimating the amplitude of noise. The sensing threshold is then adjusted dependent upon amplitude of the cardiac depolarization deflection, the number of noise deflections, and the estimated amplitude of noise detected during the predetermined portion of the period. The determination of the sensing threshold may be repeated on a beat-to-beat basis or may be repeated after a predetermined time or interval. Those skilled in the art will appreciate that the preferred embodiment may be adapted for use during either an atrial autosense or ventricular autosense mode. Determining or estimating the amplitude of noise immediately following the detected cardiac depolarization reduces the overall length of time required to adjust the sensing threshold and reduces the likelihood of malsensing a cardiac depolarization.

OBJECTS

It is accordingly a principle object of the present invention to provide a rhythm management device that automatically adjusts the sensing threshold on a beat by beat basis, such that the sensing threshold is adjusted dependant upon the amplitude of cardiac depolarization and noise.

Another object of the present invention is to provide a method of adjusting the sensing threshold dependent upon the amplitude of noise and cardiac depolarization, wherein the method may be implemented by the hardware of a conventional rhythm management device.

Still another object of the present invention is to provide a rhythm management device that adjusts the sensing threshold dependant upon the amplitude of noise and cardiac depolarization, which is operable in either a ventricular autosense or atrial autosense mode.

Yet another object of the present invention is to provide a rhythm management device that immediately adjusts the sensing threshold without an iteration of the sensing threshold level.

A further object of the present invention is to provide a rhythm management device that adjusts the sensing threshold and discriminates portions of the cardiogram signal due to noise, fibrillation, or flutter.

These and other objects and advantages of the present invention will become readily apparent to those skilled in the art from a review of the following detailed description of the preferred embodiment especially when considered in conjunction with the claims and accompanying drawings in which like numerals in the several views refer to corresponding parts.

DESCRIPTION OF THE PREFERRED EMBODIMENT

The present invention represents broadly applicable improvements to an implantable cardiac rhythm management device capable of automatically sensing intrinsic events of a patient's heart, wherein the sensing threshold is automatically adjusted as a function of intrinsic beat amplitude and noise "measured" during a predetermined period immediately following the intrinsic beat detection. The "measurement" of noise may vary depending upon the mode of autosense, for example, atrial autosense or ventricular autosense. The embodiments detailed herein are intended to be taken as representative or exemplary of those in which the improvements of the invention may be incorporated and are not intended to be limiting.

Figure 1:
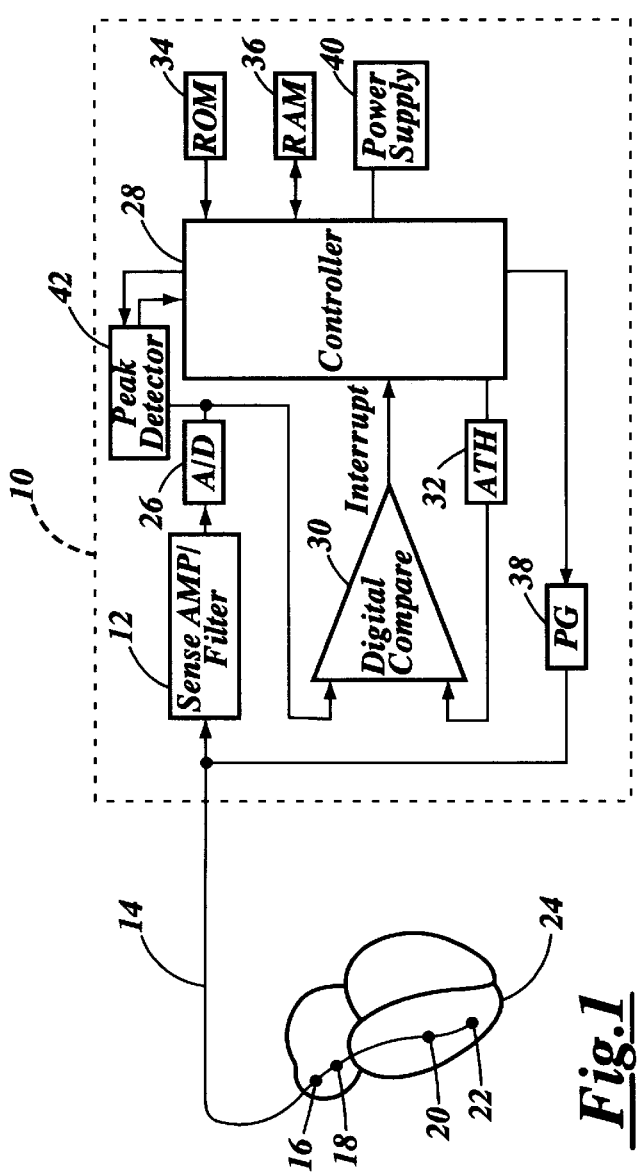
FIG. 1 is a general block diagram of a cardiac rhythm management device which may incorporate the autosense feature of the present invention.

Referring first to FIG. 1, there is illustrated by means of a block diagram, a hardware platform in which the autosense algorithm of the present invention may be utilized. Shown enclosed by the broken line box 10 is circuitry which may be included within a cardiac rhythm management device, such as a bradycardia pacemaker. It is seen to include a sense amplifier/filter 12 having its input connected by a pacing lead 14. The pacing lead 14 is shown having a plurality of electrodes 16–22 coupled to lead 14 and disposed on or in the heart 24. An electrogram signal is transmitted through the pacing lead 14 to the sense amplifier/filter 12.

In FIG. 1 the lead 14 is shown as a bipolar single pass VDD or DDD lead, various forms of which are known to those skilled in the art. Without limitation, the electrodes 20 and 22 are designed to detect ventricular depolarization while electrodes 16 and 18 sense atrial depolarization. The controller 28 is coupled to power supply 40 and provides a control output to a pulse generator 38 at appropriate times. The resulting pulses are applied over the lead 14 to the electrodes 16, 18, 20 and 22 for providing electrical stimulation to the heart 24. The arrangement shown in FIG. 1 can be used for sensing both intrinsic P-waves and R-waves as well as applied pacing pulses in the atrium and ventricle. Those skilled in the art will appreciate that the method of measuring noise while sensing intrinsic P-waves, R-waves, or applied pacing pulses may vary for atrial autosense and ventricular autosense.

The sense amp/filter circuit 12 conditions the electrogram signal and then applies the conditioned signal to an analogto-digital converter 26 which converts the conditioned signal to corresponding digital values compatible with a peak detector 42. From the analog-to-digital converter 26, the signal is transmitted to both peak detector 42 and a comparator 30. Without any limitation intended, the peak detector may include a digital comparator and register, wherein the signal transmitted from the A/D converter 26 is continuously compared with an initial value stored in the peak detector register. If the current signal is greater than the value stored in the peak detector, the current value is loaded into the register value and is then stored in the peak detector register. The peak detector 42 includes a clearing mechanism controlled by the controller 28. Those skilled in the art will recognize that timers, utilized to activate and deactivate the peak detector, may be either external or internal to the controller 28. Once the peak detector 42 times out, the final peak detector register value is transmitted to the controller 28. In this manner the peak detector 42 may be utilized to determine the amplitudes of the cardiac depolarization events and noise.

The output from the A/D converter 26 may also be applied as a first input to a digital comparator 30. A second reference input is compared by digital comparator to the first input transmitted from the A/D converter 26. The reference input of the comparator 30 is a digital value stored in the ATH register 32. The controller 28 may periodically compute and modify the digital value stored in the ATH register 32. Without limitation, the reference input of the comparator 30 may correspond to, for example, the sensing threshold. Of course, other components of suitable known construction are utilized to provide the operable cardiac rhythm management device of the present invention.

The drawing of FIG. 1 shows only one hardware configuration in which the autosense algorithm of the present invention can be implemented. Those skilled in the art can appreciate that the circuit of FIG. 1 can be modified so that, for example, the digital comparator 30 and ATH register 32 can be internal to the controller 28. It is also possible to add an additional digital comparator in parallel with the digital comparator 30 and provide a separate threshold register for corresponding sensing threshold (ST) rather than time sharing the digital comparator 30 between the detection of cardiac depolarization and noise. The controller 28 may be in any of several forms including a dedicated state device or a microprocessor with code, and may include ROM memory 34 for storing programs to be executed by the controller 28 and RAM memory 36 for storing operands used in carrying out the computations by the controller 28.

The operation of the autosense algorithm of the present invention is based upon the detection and measurement of noise during a period following a cardiac depolarization. The method of measuring noise may be modified depending upon the hardware constraints of the rhythm management device and whether the device is operating in atrial autosense or ventricular autosense. As will be described in greater detail below, during ventricular autosense, following a cardiac depolarization and during a predetermined portion of a predetermined period, the sensing threshold is reduced and the amplitude of each noise deflection is determined. During atrial autosense, following a cardiac depolarization and during a predetermined period (which may coincide with PVARP), the noise amplitude and number of deflections may be determined. In an alternate embodiment, the noise level is estimated and the number of deflections exceeding the sensing threshold is determined over a predetermined period following a cardiac depolarization. From the noise detection, the sensing threshold may be automatically adjusted by the controller 28, and updating of sensing threshold may be done on a beat-by-beat basis which may be useful and increase performance.

Figure 2:
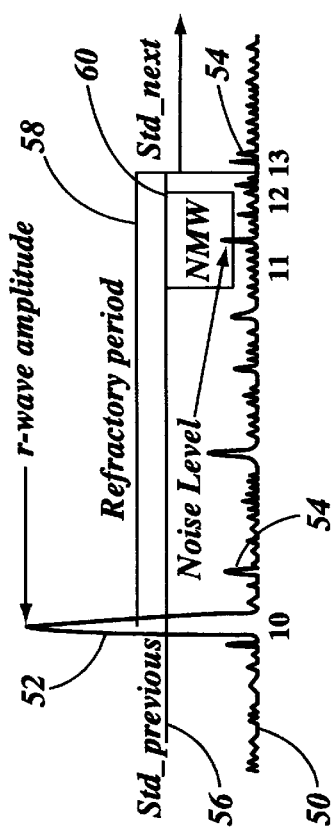
FIG. 2 is a graph of an electrogram showing the noise measurement window implemented for ventricular autosense.

Referring to FIG. 2, there is shown an electrogram signal as it relates to an implantable cardiac rhythm management device set in a ventricular autosense mode and incorporating the improvements of the present invention. The electrocardiogram signal represented by the waveform 50 includes a cardiac depolarization or r-wave deflection 52 and numerous noise deflections 54. The ventricular autosense mode is shown including a sensing threshold which is represented by line 56 and a refractory period represented by line 58. The sensing threshold 56 may be implemented to effectively block out sensing by the controller 28 all deflections in the waveform 50 that do not have an amplitude value greater than the preset sensing threshold value. As previously mentioned, a comparator may be utilized to block out all deflections that do not have an amplitude that exceeds the sensing threshold value, for example, 0.25 mV.

During ventricular autosense, once a cardiac depolarization is detected at $t_0$, a refractory period is initiated and the sensing threshold 56 is reduced for a period of time ($t_2$–$t_1$), shown as the noise measurement window (NMW) 60 during the refractory period 58, such that the maximum amplitude of noise may be detected and measured. In the preferred embodiment, the NMW ends at least 10 ms prior to the end of the refractory period ($t_3$–$t_2$), thereby reducing the likelihood that a premature ventricular contraction (PVC) will be confused as noise.

Figure 3:
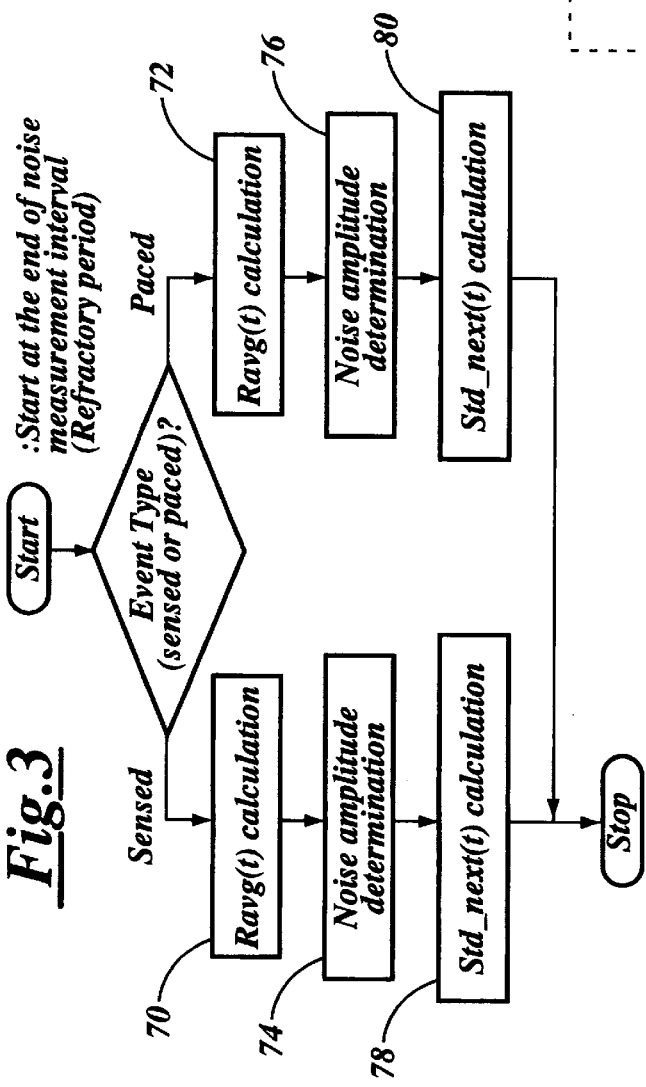
FIG. 3 is a software flow diagram of the autosense algorithm of the present invention following the measurement of noise for ventricular autosense.

Embodied in the controller 28 is a timer and deflection counter capable of measuring the number of deflections having an amplitude that exceeds the sensing threshold during each predetermined period. When the timer times out for each refractory period, the sensing threshold 56 value is adjusted by the controller 28 as a function of the measured noise and intrinsic beat. FIG. 3 shows an algorithm in flowchart form that may be implemented by the controller 28 to adjust the sensing threshold as a function of noise and intrinsic beat during ventricular autosense. This algorithm is executed by a dedicated portion of controller 28 shown in FIG. 1.

Without any limitation intended, when an electrocardiogram excursion picked up on lead 14 is signal processed by the sense amplifier/filter circuit 12 and converted to a digital quantity by A/D converter 26, a digital quantity proportional to the excursion is applied to one input of the digital comparator 30 and to the controller 28. If the electrocardiogram excursion exceeds the sensing threshold, the controller processes the signal as a cardiac depolarization, measuring the amplitude of the depolarization wave, initiating the refractory period 58 and predetermined period, and measuring the amplitude of noise deflections detected in the noise measurement window 60. Once the refractory period 58 times out, the controller 28 initiates a sequence to determine and adjust the sensing threshold 56. The sequence that the controller 28 follows will now be discussed. First, the detected cardiac depolarization or r-wave amplitude is "smoothed" or "averaged" according to the following equations:

$$Ravg(t) = \frac{1}{4}R(t) + \frac{3}{4}Ravg(t-1),$$

$$Ravg(t) = Ravg(t-1) - rm,$$

wherein the first equation is applied if the detected cardiac depolarization is intrinsic (see FIG. 3, block 70) and the second equation is applied if the detected cardiac depolarization results from pacing stimulus (see FIG. 3, block 72). R(t) is the current amplitude of the cardiac depolarization, Ravg(t−1) is the previous "smoothed" r-wave amplitude, and rm is a preselected constant that, without limitation, may range between 0.001–2.5 mV. The preselected constant, rm, will vary depending upon whether sensing in the atrial autosense or ventricular autosense mode, with 0. 14 mV being preferred for ventricular autosense and 0.03 mV being preferred for atrial autosense. Those skilled in the art will recognize and appreciate that the rm may, for convenience, be set equal to the resolution of the A/D converter 26. Once a current "smoothed" r-wave amplitude is determined, then the noise level is determined (see blocks 74 and 76) from the following equation:

$$N(t) = \text{Max}[\text{Min}(5\ mV; NWAmp); 0.375\ mV; N(t-1) - rm]$$

wherein NWAmp is the maximum amplitude of noise measured in the noise measurement window 60, N(t−1) is the previously determined noise level, and rm is a preselected constant as described previously. After the noise level and current "smoothed" r-wave amplitude are determined, then a value for the sensing threshold may be determined according to the following equation:

$$Stdnext(t) = \text{Max}\left[\frac{Ravg(t) - N(t)}{x} + N(t);\ ymV;\ zN(t)\right]$$

wherein Stdnext(t) is defined as the next sensing threshold, x is a constant ranging between 1–5 with 2 being preferred for atrial autosense and 3 being preferred for ventricular autosense. In the alternative, x may be set as a function of noise. For example, the following equation may apply:

$$x = \frac{Ravg(t)}{N(t)}$$

Likewise, x may be set equal to the current smoothed cardiac depolarization amplitude (x=Ravg(t)); y is a constant ranging between 0.05–5 mV with 0.10 mV being preferred for intrinsic atrial autosense, 0.75 mV being preferred for intrinsic ventricular autosense, 1.5 mV being preferred for paced ventricular autosense, and 0.75 mV being preferred for paced atrial autosense; and z is a constant ranging between 1.0–5.0 with 1.5 being preferred in either atrial or ventricular autosense. In this manner, the sensing threshold will be minimized without reducing the threshold below an acceptable signal to noise (SNR) ratio, thereby improving the rhythm management device's sensing performance and efficiency.

Figure 4:
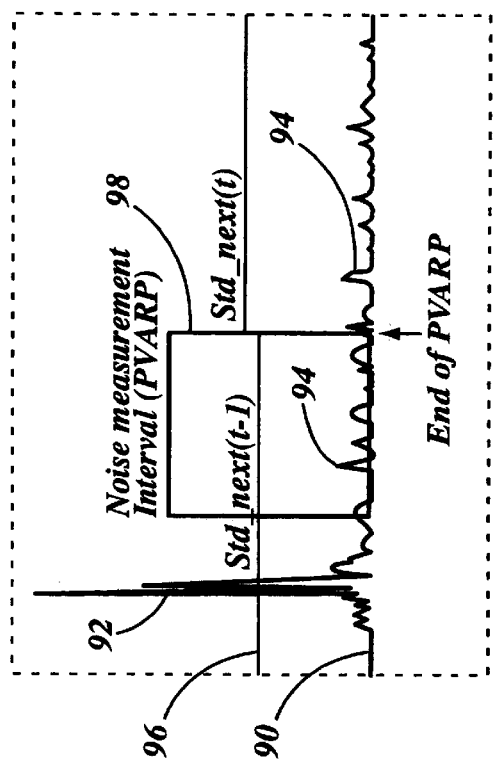
FIG. 4 is a graph of an electrogram showing the noise measurement interval implemented for atrial autosense.

Referring next to FIG. 4, there is shown generally an electrocardiogram signal typically received by an implantable cardiac rhythm management device set in an atrial autosense mode that incorporates the improvements of the present invention. The electrogram signal represented by the waveform 90 includes a cardiac depolarization or p-wave deflection 92 and numerous noise deflections 94. The atrial autosense mode includes a sensing threshold which is represented by line 96 and a post ventricular atrial refractory period or PVARP represented by line 98. Although the predetermined period or noise measurement interval is shown coinciding with the PVARP interval, those skilled in the art will appreciate that the predetermined period may be initiated prior to or after the PVARP is initiated and may be longer or shorter than the PVARP. Once a p-wave is detected by the controller 28, a timer and counter are initialized and a PVARP is executed. During PVARP, all detected deflections are presumed noise, wherein the maximum amplitude of the noise deflections is determined by the peak detector 42. A conventional RC charging circuit with a long discharging rate may also be utilized such that at the end of PVARP, the RC charging circuit should be discharged completely. Also, the number of detected deflections during the noise measurement interval are counted and the controller 28 ensures that the detected deflections are not resulting from fibrillation or atrial flutter. If the rate of detected deflections exceeds a predetermined amount, the deflections are presumed noise and the amplitude of the deflections are measured, wherein the predetermined amount may range between 300–600 deflections/minute with 500 deflections/minute being preferred. If the rate of deflections is less than the predetermined amount but greater than the Upper Rate Limit (URL-a preprogrammed maximum time that the pacer is allowed to pace) the deflections are a presumed result of atrial flutter or fibrillation.

Figure 5:
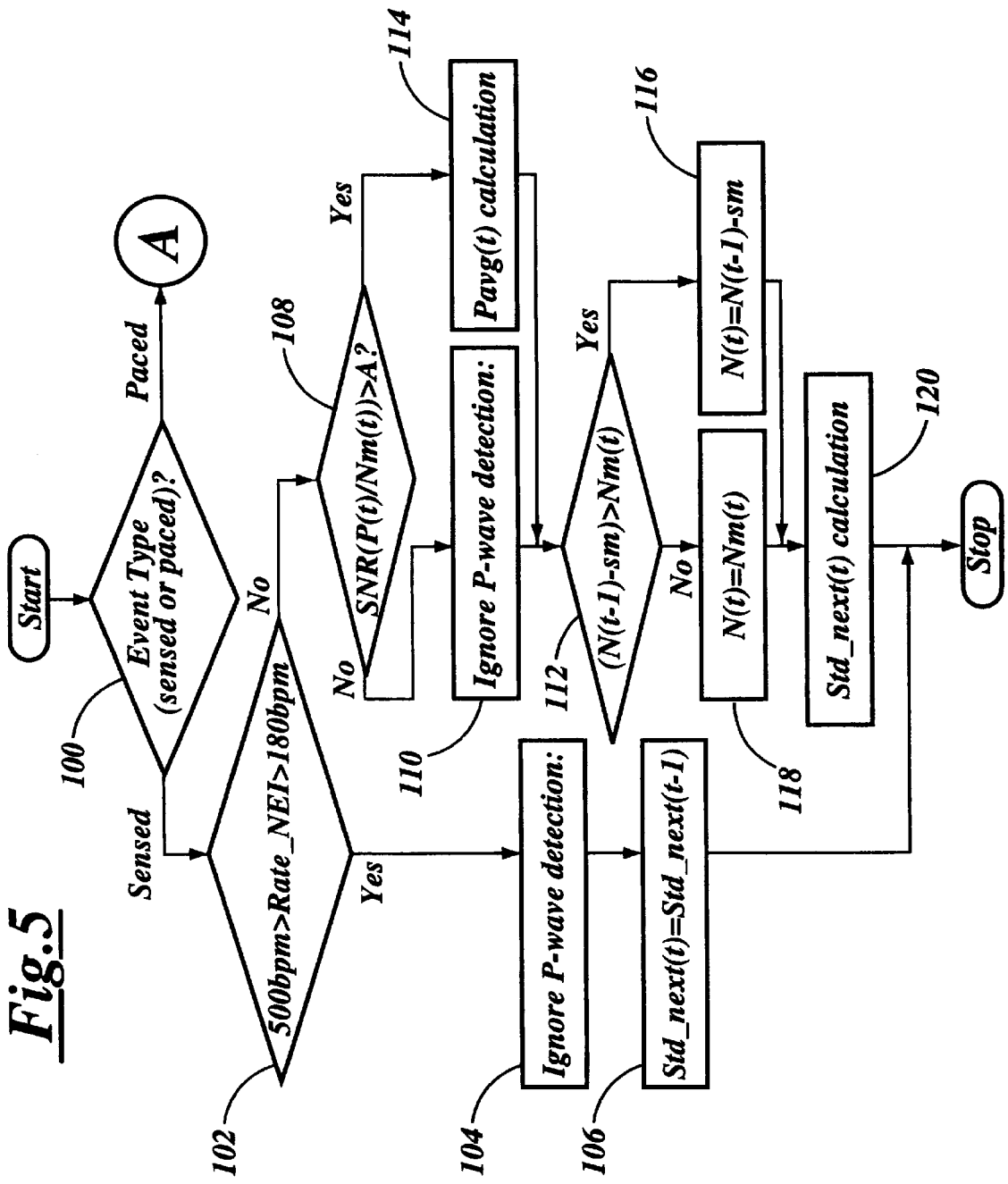
FIGS. 5 and 6 together is a software flow diagram of the autosense algorithm of the present invention following the measurement of noise for atrial autosense.

As described in greater detail below, the software utilized by the controller 28 determines a value for the sensing threshold (utilizing a comparator, for example) from the amplitude of the cardiac depolarization, the maximum amplitude of noise during the noise measurement interval, and from the quantity of noise deflections detected during a previously noise measurement interval. The algorithm that may be utilized by the controller 28 during atrial autosense varies depending upon whether the cardiac event is intrinsic or paced. Once a cardiac depolarization is detected a timer circuit and counter are initialized. At the end of the noise measurement window and PVARP, the controller 28 implements the sequence shown in FIGS. 5 and 6. For ease of discussion, the following definitions apply to the symbols used in the Figures.

Rate_NEI=rate of counted deflections during noise measurement interval exceeding the previous sensing threshold
Std_next(t)=the next sensing threshold value
Std_next(t−1)=the previous sensing threshold value
P(t)=the current p-wave amplitude
Nm(t)=measured noise amplitude within the current noise measurement interval
Pavg(t)=current smoothed p-wave amplitude value
Pavg(t−1)=previous smoothed p-wave amplitude value
N(t)=current noise level
N(t−1)=previous noise level
SNR=signal to noise ratio
sm=constant
RNW=retriggerable noise window At the end of the noise measurement interval the controller 28 implements a subroutine that first determines whether the sensed cardiac depolarization is a result of a pacing stimulus or is an intrinsic event (see decision block 100). If the cardiac depolarization is a result of a pacing stimulus, the controller 28 follows the sequence shown in FIG. 6 which is interconnected with the flowchart in FIG. 5 by connector "A". If the cardiac depolarization is a result of an intrinsic event, the controller 28 then determines the rate, in beats per minute (bpm), of the number of deflections during the noise measurement interval having an amplitude that exceeds the preceding sensing threshold level (see decision block 102). If the rate of the number of deflections is greater than 180 bpm but less than 500 bpm the p-wave detection is ignored (see block 104) and the sensing threshold value is set equal to the previous sensing threshold value (see block 106). When the rate of the number of deflections is greater than 180 bpm but less than 500 bpm, it is considered that the detected deflections are the result of atrial flutter or fibrillation. Without any limitation intended, in accordance with the above description, the predetermined lower limit may be set equal to the URL, which may preferably be set at 250 bpm.

If the rate of the number of deflections is not between 180–500 bpm then the Signal to Noise Ratio (SNR) is determined and compared to a predetermined constant A (see decision block 108). The SNR is determined by taking the measured amplitude of the p-wave cardiac depolarization and dividing by the measured noise amplitude, wherein the measured noise amplitude may be either the maximum amplitude of noise detected during the noise measurement interval or the average of all noise deflections detected during the noise measurement interval. The predetermined constant A is preferably set at 2 but may range between 1.5–5. If the SNR does not exceed the preset constant A, the p-wave detection is ignored, (see block 110) and the controller determines whether the previous noise level minus a constant "sm" exceeds the measured noise level (see decision block 112). If the SNR exceeds the preset constant A, then the current "smoothed" p-wave (Pavg(t)) is determined (see block 114) in accordance with the following:

$$Pavg(t) = \frac{1}{4}P(t) + \frac{3}{4}Pavg(t-1)$$

where P(t) is measured amplitude of the p-wave and Pavg (t−1) is the value for the previous "smoothed" p-wave. Once the Pavg(t) is determined, then the controller determines whether the previous noise level minus a constant "sm" exceeds the measured noise level (see decision block 112), where constant sm, without limitation, may range between 0.01–0.5 mV, with 0.05 mV being preferred. If the previous noise level minus constant sm exceeds the current measured noise amplitude, the noise level is set equal to the previous noise level minus the constant sm (see block 116), otherwise, the noise level is set equal to the measured noise amplitude within the current noise measurement interval (see block 118). Once a noise level value and "smoothed" p-wave value have been determined, the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 28 then sets the ATH 32, for example, equal to the calculated value and sensing continues until the next cardiac depolarization is sensed.

Figure 6:
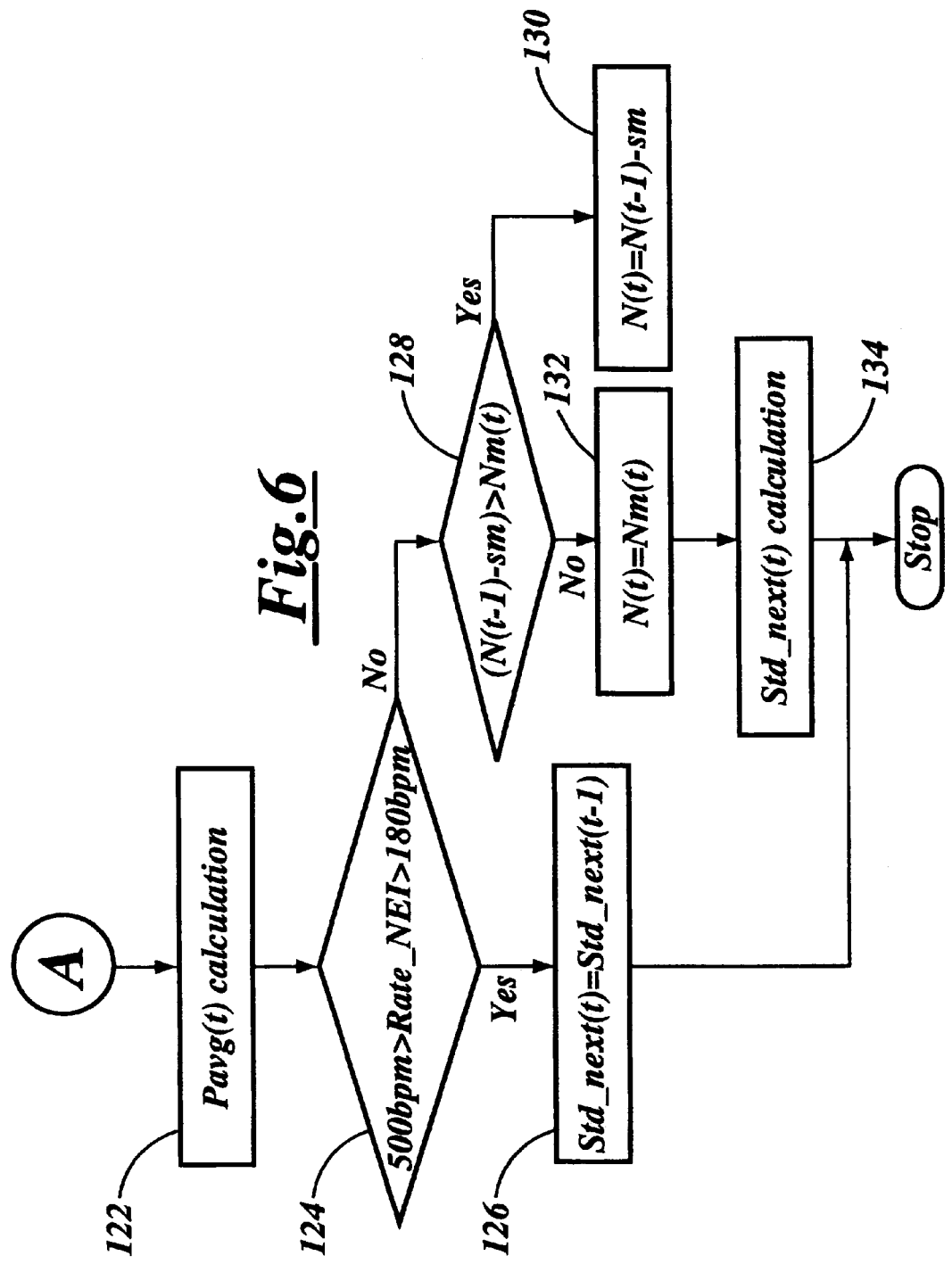

Referring again to connector "A" and FIG. 6, if the detected cardiac depolarization is the result of a pacing stimulus, following the end of the noise measurement interval the controller 28 determines the "smoothed" p-wave value (see block 122) from the following equation:

Pavg(t)=Pavg(t−1)−sm

Once a value for the "smoothed" p-wave is determined, the controller 28 then determines the rate, in beats per minute (bpm), of the number of deflections during the noise measurement interval having an amplitude that exceeds the preceding sensing threshold level (see decision block 124).

If the rate of the number of deflections is greater than 180 bpm but less than 500 bpm the next sensing threshold is set equal to the previous sensing threshold value (see block 126).

If the rate of the number of deflections is not between 180–500 bpm then the controller determines whether the previous noise level minus a constant "sm" exceeds the measured noise level (see decision block 128), where constant sm, without limitation, may range between 0.01–0.5 mV, with 0.05 mV being preferred. If the previous noise level minus constant sm exceeds the current measured noise amplitude, the noise level is set equal to the previous noise level minus the constant sm (see block 130), otherwise, the noise level is set equal to the measured noise amplitude within the current noise measurement interval (see block 132). Once a noise level value and "smoothed" p-wave value have been determined, the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 28 then sets the ATH 32, for example, equal to the calculated value and sensing continues until the next cardiac depolarization is sensed.

Figure 7:
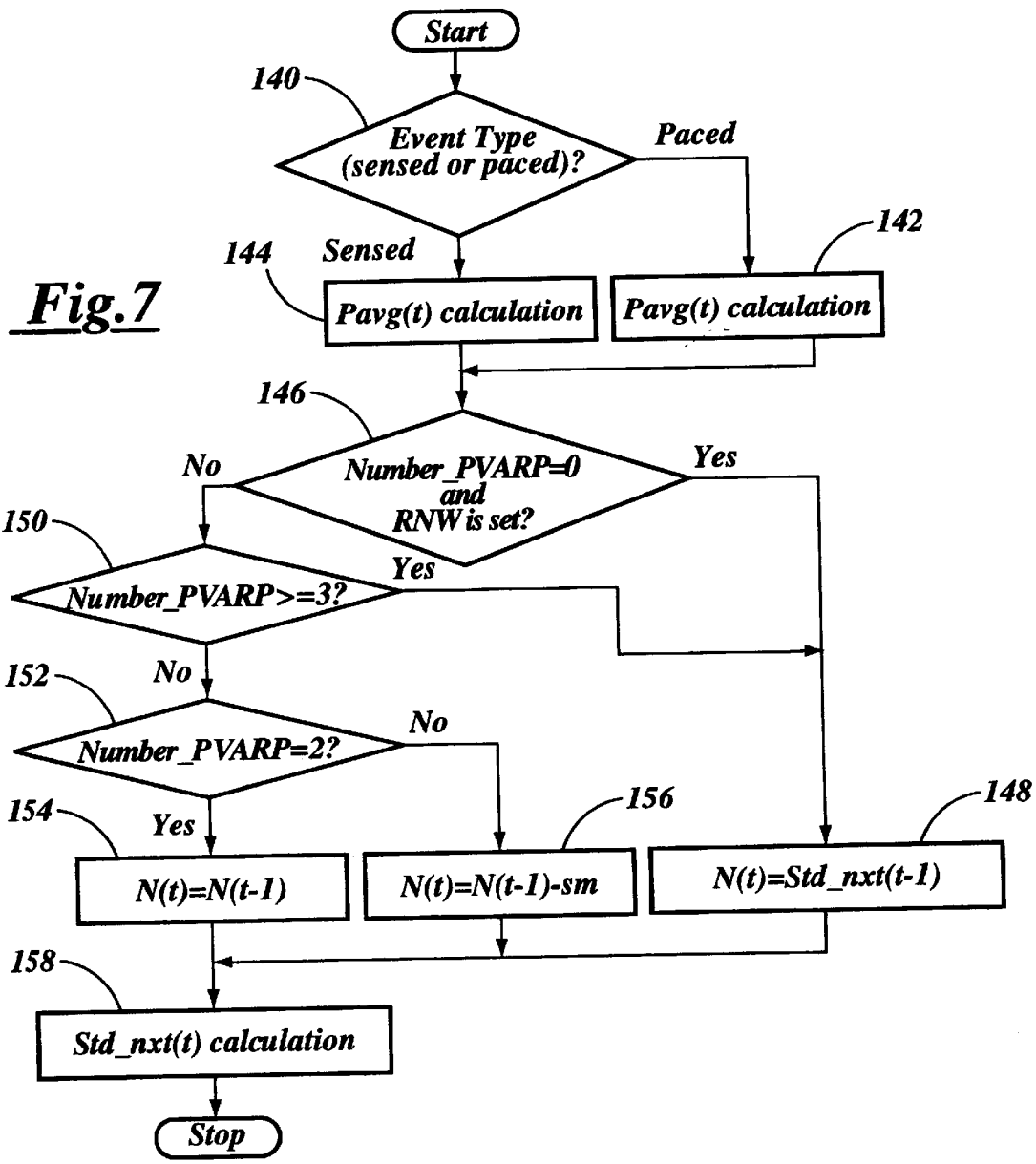
FIG. 7 is a software flow diagram of an alternate autosense algorithm of the present invention for atrial autosense.
Figure 8:
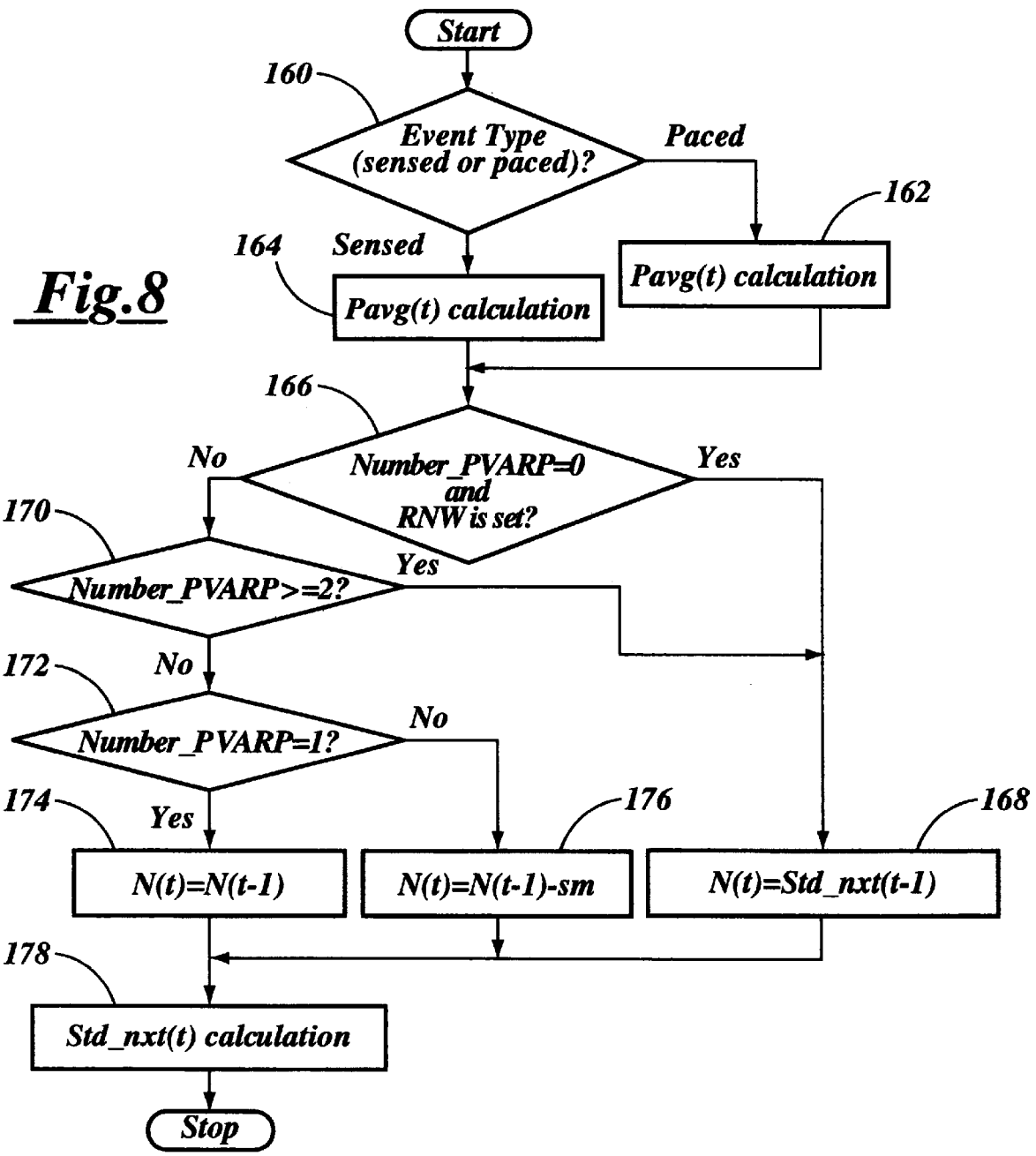
FIG. 8 is a software flow diagram of an alternate autosense algorithm of the present invention for atrial autosense.

Referring next to FIGS. 7 and 8, alternate preferred algorithms are shown that may be implemented by a cardiac rhythm management device incapable of a direct measurement of the amplitude of noise while in an atrial autosense mode. The sequence shown in FIG. 7 is implemented by the controller 28 when the PVARP is set equal to 250 ms or the PVARP exceeds 250 ms. The sequence shown in FIG. 8 is implemented when the PVARP is less than 250 ms. In the case where PVARP exceeds 250 ms, the "smoothed" p-wave amplitude and the number of events exceeding the sensing threshold is determined over a preset period (250 ms) of time or noise measurement interval within the PVARP interval.

The sequence shown in FIG. 7 is implemented by the controller after the noise measurement interval or PVARP times out. The controller 28 then determines whether the current cardiac depolarization is a result of a paced or intrinsic event (see decision block 140). If the cardiac depolarization is the result of a paced stimulus the controller 28 calculates the "smoothed" amplitude (see block 142) for the detected p-wave deflection in accordance with the following equation:

Pavg(t)=Pavg(t−1)−sm where, without limitation, sm is a constant ranging between 0.01–0.5 mV, with 0.05 mV being preferred. If the cardiac depolarization is the result of a sensed stimulus the controller 28 calculates the "smoothed" amplitude (see block 144) for the detected p-wave deflection in accordance with the following equation:

$$Pavg(t) = \frac{1}{4}P(t) + \frac{3}{4}Pavg(t-1)$$

as previously described. The controller then determines the number of deflections counted exceeding the sensing threshold during the predetermined period. If there were no deflections detected during the noise measurement interval and the retriggerable noise window of 40 ms, for example, is set (see decision block 146), then the noise amplitude value is set equal to the previous sensing threshold value (see block 148). If deflections are detected during the noise measurement interval, and the number of detected deflections exceed 3 (see decision block 150), then the noise amplitude value is set equal to the previous sensing threshold value (see block 148). If the number of detected deflections equals 2 (see decision block 152), then the value for the amplitude of noise is set equal to the previous amplitude of noise value (see decision block 154), otherwise, the amplitude of noise value is set equal to the previous value for the amplitude of noise minus a constant "sm" as previously described (see block 156). In this manner the measured amplitude of noise is estimated for the current noise measurement interval. Once the "smoothed" amplitude of the p-wave deflection and the amplitude of noise are calculated, then the value for the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 28 then sets the ATH register 32, for example, equal to the calculated value and sensing continues until the next cardiac depolarization is sensed.

As previously indicated, the sequence shown in FIG. 8 is implemented by the controller 28 after the noise measurement interval or predetermined period times out and when the PVARP is less than 250 ms. When this is the case, the controller 28 determines whether the current cardiac depolarization is a result of a paced or intrinsic event (see decision block 160). If the cardiac depolarization is the result of a paced stimulus the controller 28 calculates the "smoothed" amplitude (see block 162) for the detected p-wave deflection in accordance with the following equation:

$$Pavg(t) = Pavg(t-1) - sm$$

where, without limitation, sm is a constant ranging between 0.01–0.5 mV, with 0.05 mV being preferred. If the cardiac depolarization is the result of a sensed stimulus the controller 28 calculates the "smoothed" amplitude (see block 164) for the detected p-wave deflection in accordance with the following equation:

$$Pavg(t) = \frac{1}{4}P(t) + \frac{3}{4}Pavg(t-1)$$

as previously described. The controller then determines the number of deflections counted exceeding the sensing threshold during the PVARP interval. If there were no deflections detected during the noise measurement interval and the retriggerable noise window of 40 ms, for example, is set (see decision block 166), then the noise amplitude value is set equal to the previous sensing threshold value (see block 168). If deflections are detected during the noise measurement interval, and the number of detected deflections exceed 2 (see decision block 170), then the noise amplitude value is set equal to the previous sensing threshold value (see block 168). If the number of detected deflections equals 1 (see decision block 172), then the value for the amplitude of noise is set equal to the previous amplitude of noise value (see decision block 174), otherwise, the amplitude of noise value is set equal to the previous value for the amplitude of noise minus a constant "sm" as previously described (see block 176). In this manner the measured amplitude of noise is estimated for the current noise measurement interval. Once the "smoothed" amplitude of the p-wave deflection and the amplitude of noise are calculated, then the value for the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 28 then sets the ATH register 32, for example, equal to the calculated value and sensing continues until the next cardiac depolarization is sensed.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable cardiac rhythm management device capable of automatically sensing intrinsic events of a patient's heart and having an adjustable sensing threshold, said device including:

(a) a pulse generator;
   (b) a controller for controlling activation of the pulse generator;
   (c) conduction means for conducting an electrocardiogram signal which includes electrical impulses corresponding to cardiac depolarization and noise;
   (d) detecting means coupled to the conduction means for detecting intrinsic events from the signal;
   (e) measuring means for at least estimating an amplitude of the noise during a period following detected intrinsic events and memory means for storing the estimated amplitude of noise over a plurality of detected intrinsic events; and
   (f) adjusting means for adjusting the sensing threshold dependant upon the amplitude of noise estimated from the detected plurality of intrinsic events.

2. The implantable cardiac rhythm management device as recited in claim 1, further including a discriminating means for discriminating, from the electrocardiogram signal, electrical impulses associated with a tachyrhythmia of the patient's heart.

3. The implantable cardiac rhythm management device as recited in claim 1, wherein the amplitude of the noise is measured for a predetermined period of time following detection of cardiac depolarization.

4. The implantable cardiac rhythm management device as recited in claim 1, wherein the measurement of the amplitude of noise is initiated by a detection of cardiac depolarization resulting from an intrinsic event in an atrium of the patient's heart.

5. The implantable cardiac rhythm management device as recited in claim 1, wherein the measurement of the amplitude of noise is initiated by a detection of cardiac depolarization resulting from an intrinsic event in a ventricle of the patient's heart.

6. The implantable cardiac rhythm management device as recited in claim 1, further including memory means for storing the measured amplitude of noise over a plurality of detected cardiac depolarization and adjusting the sensing threshold dependent upon the measured amplitude of noise corresponding to prior detected cardiac depolarization.

7. The implantable cardiac rhythm management device as recited in claim 1, further including a means for averaging the amplitude over a preset period of time.

8. The implantable cardiac rhythm management device as recited in claim 1, further including means for determining the maximum amplitude of noise over a preset period of time.

9. An implantable cardiac rhythm management device capable of automatically sensing intrinsic events of a patient's heart and having an adjustable sensing threshold, said device including:

(a) a pulse generator;

(b) a controller for controlling activation of the pulse generator;

(c) conduction means for conducting electrogram signals including electrical impulses corresponding to cardiac depolarization and noise;

(d) detecting means coupled to said conduction means for detecting deflections in the electrogram signal corresponding to intrinsic cardiac events;

(e) measuring means for measuring at least one of an amplitude of noise, a number of deflections in the signal over a predetermined period, and a number of deflections in the signal exceeding a current sensing threshold over a preset period and including means for determining the maximum amplitude of noise over a preset period of time; wherein the measuring occurs during a period following detected cardiac depolarization; and (f) adjusting means for adjusting the current sensing threshold dependant upon at least one of the measured amplitude of noise, the measured number of deflections in the signal over a predetermined period, and the measured number of deflections in the signal exceeding the current sensing threshold.

10. The implantable cardiac rhythm management device as recited in claim 9, further including a discriminating means for discriminating the detected deflections from a tachyrhythmia of the patient's heart.

11. The implantable cardiac rhythm management device as recited in claim 9, wherein at least one of the amplitude of the noise, the number of deflections in the signal over the predetermined period and the number of deflections in the signal exceeding the current sensing threshold, is measured during a predetermined portion of the period.

12. The implantable cardiac rhythm management device as recited in claim 9, wherein the period is initiated by a detection of cardiac depolarization resulting from an intrinsic event in an atrium of the patient's heart.

13. The implantable cardiac rhythm management device as recited in claim 9, wherein the period is initiated by a detection of cardiac depolarization resulting from an intrinsic event in a ventricle of the patient's heart.

14. The implantable cardiac rhythm management device as recited in claim 9, further including means for averaging the amplitude of noise over a preset period of time.

15. A method of automatically adjusting a sensing threshold in a cardiac rhythm management device in order to distinguish cardiac depolarization events from noise in a cardiac electrogram signal, the cardiac rhythm management device being of the type having means for sensing intrinsic events, a controller, and means controlled by the controller for applying cardiac stimulation pulses to a patient's heart on a beat-to-beat basis, said method including the steps of:

(a) setting the sensing threshold to a predetermined value;

(b) sensing signals comprising electrical impulses corresponding to cardiac depolarization and noise;

(c) detecting from the sensed signal intrinsic cardiac events and noise;

(d) measuring an amplitude of the noise during a period following detected intrinsic cardiac events and storing the measured amplitude of noise over a plurality of detected intrinsic cardiac events;

(e) adjusting the sensing threshold dependant upon the measured amplitude of the noise over the plurality of detected intrinsic cardiac events.

16. The method as recited in claim 15, further including the step of discriminating the detected noise from a tachyrhythmia prior to adjusting the sensing threshold.

17. The method as recited in claim 15, wherein the measurement of the amplitude of noise is initiated by detecting a cardiac depolarization resulting from an intrinsic event in an atrium of the patient's heart.

18. The method as recited in claim 15, wherein the measurement of the amplitude of noise is initiated by detecting a cardiac depolarization resulting from an intrinsic event in a ventricle of the patient's heart.

19. The method as recited in claim 15, further including the step of storing the measured amplitude of noise over a plurality of detected cardiac depolarizations prior to adjusting the threshold and then adjusting the sensing threshold dependant upon the measured amplitude of noise from prior detected cardiac depolarization.

20. The method as recited in claim 15, wherein the measured amplitudes of noise, measured for the predetermined period of time, are averaged and the average amplitude of noise is used to adjust the sensing threshold.

21. The method as recited in claim 15, wherein the measured amplitudes of noise, measured for the preset period of time, are maximized and the maximum measured amplitude of noise is used to adjust the sensing threshold.

* * * * *